United States Patent [19]

Schalenbach et al.

[11] Patent Number: 4,661,646
[45] Date of Patent: Apr. 28, 1987

[54] PROCESS FOR THE PREPARATION OF 1-BUTENE-3,4-DIOL

[75] Inventors: Rolf Schalenbach, Cologne; Helmut Waldmann, Leverkusen, both of Fed. Rep. of Germany

[73] Assignee: Bayer Aktiengesellschaft, Leverkusen, Fed. Rep. of Germany

[21] Appl. No.: 800,495

[22] Filed: Nov. 21, 1985

Related U.S. Application Data

[63] Continuation of Ser. No. 652,794, Sep. 20, 1984, abandoned.

[30] Foreign Application Priority Data

Sep. 24, 1983 [DE] Fed. Rep. of Germany ....... 3334589

[51] Int. Cl.$^4$ ..................... C07C 29/56; C07C 33/035
[52] U.S. Cl. ................................. 568/857; 568/868; 568/921
[58] Field of Search ................................ 568/857, 906

[56] References Cited

U.S. PATENT DOCUMENTS

| | | | |
|---|---|---|---|
| 2,911,445 | 11/1959 | Friederich | 568/857 |
| 2,961,471 | 11/1960 | Hort | 568/857 |
| 3,642,919 | 2/1972 | Bonnetti et al. | 568/857 |
| 4,160,115 | 7/1979 | Vasey et al. | 508/857 |

FOREIGN PATENT DOCUMENTS

| | | | |
|---|---|---|---|
| 2414341 | 10/1975 | Fed. Rep. of Germany | 568/857 |
| 2227 | 1/1982 | Japan | 568/857 |
| 2096595 | 10/1982 | United Kingdom | 568/857 |

Primary Examiner—J. E. Evans
Attorney, Agent, or Firm—Sprung Horn Kramer & Woods

[57] ABSTRACT

1-Butene-3,4-diol is prepared by heat treatment of 2-butene-1,4-diol in the presence of catalytically active substances under acid conditions.

16 Claims, No Drawings

PROCESS FOR THE PREPARATION OF 1-BUTENE-3,4-DIOL

This is a continuation of application Ser. No. 652,794, filed Sept. 20, 1984, now abandoned.

The present invention relates to a new process for the preparation of 1-butene-3,4-diol.

Unsaturated C4-diols are of economic interest as intermediates for active compounds and as parent compounds for polymers (see Ullmanns Enzyclopädie der technischen Chemie (Ullmann's Encyclopaedia of Industrial Chemistry), 4th edition, Volume 9, page 19; Kirk-Othmer, Encyclopedia of Chemical Technology, 3rd edition, Vol. 1, page 256 (1978)). Furthermore it is known to use 1-butene-3,4-diol as an antidiscoloration agent for molded articles and coating compositions (see German Offenlegungsschrift No. 25 02 218).

1-Butene-3,4-diol has hitherto been prepared by, for example, the hydrogenation of polymeric peroxides of butadiene (see U.S. Pat. No. 4,209,651 and U.S. Pat. No. 2,898,377). The disadvantages of this procedure are the low yields in which polymeric peroxides can be obtained by oxidation of butadiene, and the formation of a mixture of the 1,2- and 1,4-adducts (see U.S. Pat. No. 3,023,249; C. T. Handy, H. S. Rothrock, J. Am. Chem. Soc. 80, 5306 (1958)).

Another route to 1-butene-3,4-diol is the hydrolysis of vinyloxirane (see Japanese Offenlegungsschrift No. 79/79214; W. F. Whitmore, J. Am. Chem. Soc. 71, 2427 (1949)). This procedure has the disadvantage that vinyloxirane is not at present available in industrial amounts and has first to be prepared from butadiene.

Furthermore, 1-butene-3,4-diol can be obtained by the hydrolysis of 3,4-diacetoxybutene which results as a by-product of the acetoxylation of butadiene to give 1,4-diacetoxy-2-butene (see German Offenlegungsschrift No. 3,022,288). A difficulty with carrying out this procedure is that 3,4-diacetoxy-2-butene results in only small amounts, and the separation of the isomeric diacetates is difficult.

2-Butene-1,4-diol, which is the structural isomer of 1-butene-3,4-diol, is available on an industrial scale by the hydrogenation of 2-butine-1,4-diol (see U.S. Pat. No. 4,213,000; German Offenlegungsschrift No. 2,605,241; German Offenlegungsschrift No. 2,431,929), which can be prepared by a known reaction of acetylene and formaldehyde (see U.S. Pat. No. 3,560,576; U.S. Pat. No. 3,920,759; German Offenlegungsschrift No. 2,314,693). The rearrangement of 2-butene-1,4-diol to 1-butene-3,4-diol would make it possible to obtain 1-butene-3,4-diol, by a straightforward route and without the formation and isolation of intermediates, starting from 2-butine-1,4-diol which is available on an industrial scale.

It is in fact known in principle that isomerization reactions can be carried out on compounds having an allyl alcohol structure (see C. Ferri, Reaktionen der organischen Chemie (Reactions of Organic Chemistry), published by Georg Thieme, 1978, page 243). However, the rearrangements of allyl alcohols frequently do not take place in the desired manner. If reactions of this type are carried out in the gas phase, the unsaturated alcohols isomerize to give the corresponding aldehydes and ketones (see M. Kraus, Coll. Czech. Chem. Commun. 37, 460 (1972); G. Eadon, M. Y. Sheikh, J. Am. Chem. Soc. 96, 2288 (1974)).

Allyl alcohols can be rearranged in the liquid phase with retention of the hydroxyl group on treatment with acid (see Braude, Quart. Rev. 4, 407 (1950)). It is known, from U.S. Pat. No. 2,373,956, that 3-pentene-1,2-diol is converted into 2-pentene-1,4-diol on heating in dilute sulphuric acid.

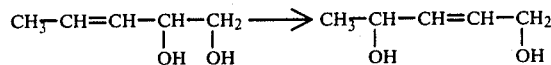

This is the reverse process to that which is desired for the isomerization of 2-butene-1,4-diol to 1-butene-3,4-diol.

The reaction of 2-butene-1,4-diol with CuCl2 in the absence of acids is described in German Patent Specification No. 961,353. 1,4-Divinyldioxane is formed on heating 2-butene-1,4-diol under reflux in the presence of CuCl2.

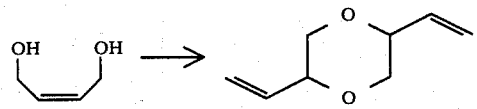

The processes which have hitherto become known for the preparation of 1-butene-3,4-diol are thus not suitable for industrial preparation and, according to the relevant state of the art, it was not to be expected that 2-butene-1,4-diol can be rearranged to give 1-butene-3,4-diol.

A process for the preparation of 1-butene-3,4-diol has now been found, which is characterised in that 2-butene-1,4-diol is heat-treated in the presence of catalytically active substances under acid conditions.

In principle, any 2-butene-1,4-diol is suitable for carrying out the process according to the invention, for example an industrial product which has been prepared by hydrogenation of 2-butene-1,4-diol.

Examples of catalytically active substances for the process according to the invention are the elements of the 3rd and 4th main groups of the Mendeleev periodic table of the elements, and the transition metals, as well as compounds of these elements and compounds of transition metals. Boron, aluminium, tin, lead, copper, zinc, iron, silver, cadmium, ruthenium, palladium, gold and mercury and their compounds are preferred. Elements of the 1st and 2nd sub-groups of the Mendeleev periodic table of the elements and their compounds are particularly preferred, and copper and its compounds are very particularly preferred.

Examples of suitable compounds of the abovementioned elements and transition metals are those which contain oxygen, nitrogen, sulphur, phosphorus, halogen and/or carbon, for example oxides, nitrates, sulphates, phosphates, fluorides, chlorides, bromides, iodides, perchlorates, acetates, trifluoroacetates and the like.

Examples of specific compounds which are preferred are $BF_3$, $AlCl_3$, $SnCl_2$, $SnCl_4$, $Pb(acetate)_2$, $CuSO_4$, $Cu(NO_3)_2$, $Cu(acetate)_2$, $CuCl_2$, $CuCl$, $CuI$, $CuBr$, $ZnCl_2$, $HgCl_2$, $AgClO_4$, $AgO_2CCF_3$, $FeCl_2$, $FeCL_3$, $CdBr_2$, $Pd(acetate)_2$, $PdCl_2$, $AuCl_3$ and $RuCl_3$.

Compounds of copper are particularly preferred, in particular those of monovalent copper, such as CuCl, CuBr and CuI, but CuCl is very particularly preferred.

It is not crucial for the process according to the invention whether the abovementioned elements and compounds are used as such, are first formed under the process conditions, or are converted during the process.

The amount of the catalytically active substances in the process according to the invention can be varied within wide limits. For example, relative to the 2-butene-1,4-diol used, they can be used in amounts between 0.1 and 25% by weight, preferably in amounts between 1 and 10% by weight, and particularly preferably in amounts between 2 and 5% by weight. These limits are guidelines which can be fallen short of or exceeded.

When the catalytically active substances have an acid action, for example because they are Lewis acids, there is no need to adopt special measures for setting up acid conditions for carrying out the process according to the invention. Where acid conditions have first to be set up, as well as in addition to catalytically active substances having an acid action, it is possible to use acids in the isomerization according to the invention. In principle, both organic and inorganic acids are suitable, for example formic acid, acetic acid, trifluoroacetic acid, phosphoric acid, hydrochloric acid, sulphuric acid and perchloric acid, as well as acid ion exchangers. Hydrochloric acid and sulphuric acid are preferred, in particular hydrochloric acid.

The amount of acid, which is to be added where appropriate, can be varied within wide limits. Thus, relative to 2-butene-1,4-diol used, the amount can be, for example, 0.5–40% by weight. In this context, an amount of 5–30% by weight is preferred, and one of 10–25% by weight is particularly preferred. The limits indicated can also be fallen short of or exceeded.

It can be advantageous to carry out the process according to the invention in the presence of a solvent. Examples of suitable solvents are alcohols, ethers, polyethers, esters, acids and water. It is advantageous to use those solvents whose boiling points are in the region of the temperature necessary for the heat treatment. Preferred solvents are ethanol, water, dimethoxyethane and acetic acid. Water is particularly preferred. The amount of the solvent can be vaired within a wide range. Thus, relative to 2-butene-1,4-diol used, solvents can be used in, for example, 0.1–20 times the amount by weight. In this context, 1–12 times is preferred, and 2–10 times the amount is particularly preferred.

Within the meaning of the present invention, heat treatment is to be understood to be intimate contact of the reaction mixture at an adequate temperature. In general, adequate temperatures for the process according to the invention are as low as 50°–60° C. It is advantageous, in order to achieve a higher rate of reaction, to work at higher temperatures, for example at 60°–150° C. It is also possible to use higher temperatures, for example those up to 190° C. and above. Temperatures of 80°–120° C. are particularly preferred.

Intimate contact of the reaction mixture can be achieved by, for example, stirring.

The lengths of the residence times necessary to achieve good yields will vary depending on whether the process according to the invention is carried out at a higher or lower temperature. In general, shorter residence times are possible at a higher temperature than at a lower temperature to achieve good yields. In general, the residence times are in the range 1–15 hours.

Pressure is of subordinate importance for carrying out the process according to the invention. It will normally be carried out under atmospheric pressure. However, it is also possible to carry it out under elevated or reduced pressure.

The 1-butene-3,4-diol can be isolated by distillation, where appropriate by distillation under reduced pressure, out of the reaction mixture resulting after the process according to the invention has been carried out. In order to avoid decomposition during distillation, it is advantageous to neutralize the reaction mixture before distillation and, where appropriate, then to filter off precipitated solids.

The process according to the invention can be carried out continuously or discontinuously. Examples of suitable reaction vessels are stirred reactors or cascades of stirred reactors. Examples of suitable materials for the reaction vessels are stainless steels, glass, enamel, tantalum and titanium.

In a preferred embodiment of the process according to the invention, 2-butene-1,4-diol, which has been obtained from the hydrogenation of 2-butine-1,4-diol, is mixed with a solvent, an acid and a catalytically active substance in a stirred vessel. Then the reaction mixture is heated to the desired temperature and is stirred. After neutralization and, where appropriate, removal of precipitated solids, 1-butene-3,4-diol is isolated by distillation.

The process according to the invention is illustrated in more detail by means of the examples which follow, without restricting it in any manner.

EXAMPLE 1

50 g of 2-butene-1,4-diol were dissolved in 250 ml of water and, after addition of 10 ml of 37% strength aqueous hydrochloric acid and 2 g of CuCl, the mixture was heated at 90° C. for 2 hours (internal temperature) and stirred during this. Analysis of the crude product by gas chromatography showed a content of 8.5% by weight of 1-butene-3,4-diol and 6.3% by weight of 2-buten-1,4-diol. This corresponds to a 61% conversion of 2-butene-1,4-diol and a selectivity for 1-butene-3,4-diol of 85%.

EXAMPLE 2

100 g of 2-butene-1,4-diol were dissolved in 600 ml of water and, after addition of 5 ml of concentrated aqueous hydrochloric acid and 1 g of CuCl, the mixture was heated at 100° C. After stirring for 15 hours, the reaction mixture contained 48 g of 1-butene-3,4-diol. 74% of the 2-butene-1,4-diol used had been converted.

EXAMPLE 3

9,500 ml of water were added to 1,900 g of 2-butene-1,4-diol in a stirred vessel. After addition of 380 ml of aqueous hydrochloric acid (30% by weight) and 76 g of CuCl, the reaction mixture was heated to boiling. After stirring at this temperature for 2 hours, the reaction mixture contained 790 g of 1-butene-3,4-diol. For the isolation of the 1-butene-3,4-diol, the reaction mixture was neutralized with sodium hydroxide solution, and precipitated solids were removed by filtration. Working up of the remaining mixture by distillation under reduced pressure (1 mbar) provided 776 g of 1-butene-3,4-diol, corresponding to an amount of 98% of the 1-butene-3,4-diol present in the crude product.

EXAMPLE 4

55 g of 2-butene-1,4-diol were dissolved in 250 ml of water and, after addition of 2 g of $HgCl_2$ and 10 ml of aqueous hydrochloric acid (37% strength), the mixture was heated under gentle reflux with stirring.

After 11 hours, 58% of the 2-butene-1,4-diol used had been converted. The selectivity for 1-butene-3,4-diol was 82%.

What is claimed is:

1. In a process for preparing 1-butene-3,4-diol which comprises the isomerization of 2-butene-1,4-diol wherein said 2-butene-1,4-diol is heated in the presence of a catalytically active substance under acid conditions wherein said acid is selected from the group consisting of formic acid, acetic acid, trifluoroacetic acid, phosphoric acid, hydrochloric acid, sulfuric acid, perchloric acid and an acid ion exchanger and, wherein the improvement comprises performing said isomerization in the presence of a catalytically active substance selected from the group consisting of copper, $CuSO_4$, $Cu(NO_3)_2$, $Cu(acetate)_2$, $CuCl_2$, CuCl, CuI and CuBr.

2. A process according to claim 1 wherein the process is carried out at 50° to 190° C.

3. A process according to claim 1 wherein the process is carried out in the presence of a solvent.

4. A process according to claim 1 wherein the catalytically active substance is employed in an amount of 0.1 to 25% by weight, based upon the weight of said 2-butene-1,4-diol.

5. A process according to claim 1 wherein the process is carried out in the presence of 0.5 to 40% by weight of an acid, the weight of the acid being based upon the weight of 2-butene-1,4-diol.

6. A process according to claim 1 wherein the catalytically active substance is CuCl.

7. A process according to claim 6 wherein the process is carried out employing hydrochloric acid as the acid.

8. A process according to claim 7 wherein said hydrochloric acid is in the form of aqueous hydrochloric acid.

9. A process according to claim 1, wherein said substance is selected from the group consisting of CuCl, CuBr and CuI.

10. A process according to claim 1, wherein the catalytically active substance is employed in an amount of 1 to 10% by weight, based upon the weight of said 2-butene-1,4-diol.

11. A process according to claim 1, wherein the catalytically active substance is employed in an amount of 2 to 5% by weight, based upon the weight of said 2-butene-1,4-diol.

12. A process according to claim 1, wherein the process is carried out in the presence of 5 to to 30% by weight of an acid based upon the weight of said 2-butene-1,4-diol.

13. A process according to claim 1, wherein the process is carried out in the presence of 10 to 25% by weight of an acid based upon the weight of said 2-butene-1,4-diol.

14. A process according to claim 1, wherein the process is carried out for a residence time of 1 to 15 hours.

15. A process according to claim 1, wherein the process is carried out at 80° to 120° C.

16. A process according to claim 3, wherein said solvent is in an amount of 0.1 to 20 times the amount of 2-butene-1,4-diol.

* * * * *